(12) United States Patent
Hamada

(10) Patent No.: US 8,591,420 B2
(45) Date of Patent: Nov. 26, 2013

(54) ULTRASOUND IMAGING APPARATUS AND METHOD FOR ACQUIRING ULTRASOUND IMAGE

(75) Inventor: Kenji Hamada, Otawara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 822 days.

(21) Appl. No.: 12/520,990

(22) PCT Filed: Sep. 7, 2007

(86) PCT No.: PCT/JP2007/000977
§ 371 (c)(1),
(2), (4) Date: Jun. 24, 2009

(87) PCT Pub. No.: WO2008/081558
PCT Pub. Date: Jul. 10, 2008

(65) Prior Publication Data
US 2010/0030079 A1 Feb. 4, 2010

(30) Foreign Application Priority Data
Dec. 28, 2006 (JP) .................. 2006-353931

(51) Int. Cl.
*A61B 8/14* (2006.01)

(52) U.S. Cl.
USPC ........................................ 600/443

(58) Field of Classification Search
USPC .................. 600/637, 407, 443; 382/100
See application file for complete search history.

(56) References Cited

U.S. PATENT DOCUMENTS

| | | | |
|---|---|---|---|
| 5,911,691 A | 6/1999 | Mochizuki et al. | |
| 5,934,288 A * | 8/1999 | Avila et al. | 600/443 |
| 6,241,675 B1 * | 6/2001 | Smith et al. | 600/443 |
| 2005/0240104 A1 * | 10/2005 | Shim et al. | 600/437 |
| 2006/0058605 A1 * | 3/2006 | Deischinger et al. | 600/407 |
| 2008/0044054 A1 * | 2/2008 | Kim et al. | 382/100 |

FOREIGN PATENT DOCUMENTS

| | | |
|---|---|---|
| JP | 6 343632 | 12/1994 |
| JP | 9 308631 | 12/1997 |
| JP | 2000-135217 | 5/2000 |
| JP | 2004-275223 | 10/2004 |
| JP | 2006 218210 | 8/2006 |
| JP | 2006 223712 | 8/2006 |
| JP | 2006-271523 | 10/2006 |

OTHER PUBLICATIONS

Japanese Office Action issued May 29, 2012, in Japan Patent Application No. 2007-238217.

* cited by examiner

*Primary Examiner* — Sanjay Cattungal
*Assistant Examiner* — Lawrence Laryea
(74) *Attorney, Agent, or Firm* — Oblon, Spivak, McClelland, Maier & Neustadt, L.L.P.

(57) ABSTRACT

An ultrasound imaging apparatus capable of easily displaying a three-dimensional image included in a region of interest (ROI). A display controller causes a display to display a tomographic image, and further causes the display to display a first marker indicating a three-dimensional scan range and a second marker indicating a range to generate three-dimensional image data, a range subjected to rendering, to be superimposed on a tomographic image. The second marker is rotatable on the tomographic image in accordance with an instruction by an operator. A transceiver causes an ultrasound probe to scan the three-dimensional scan range specified based on the first marker. An image processor executes rendering on, of data acquired in the scan, data included in the range specified based on the second marker, thereby generating three-dimensional image data.

14 Claims, 10 Drawing Sheets

TRANSMISSION/RECEPTION DIRECTION

TRANSMISSION/RECEPTION DIRECTION

TRANSMISSION/RECEPTION DIRECTION

ULTRASOUND IMAGING APPARATUS AND METHOD FOR ACQUIRING ULTRASOUND IMAGE

TECHNICAL FIELD

The present invention relates to an ultrasound imaging apparatus that acquires a three-dimensional image of an observation object, and also relates to a method for acquiring an ultrasound image.

BACKGROUND ART

An ultrasound imaging apparatus capable of generating and displaying three-dimensional image data of a subject is known.

A three-dimensional image is generated by an image processing method such as volume rendering, and displayed on a screen. However, when an unnecessary part exists around a region to observe (a region of interest (ROI)), the unnecessary part is an obstacle and makes it difficult to observe a three-dimensional image included in the region of interest. Thus, in conventional arts, an unnecessary image, which is not included in a region of interest, is removed. For example, while a range to display a three-dimensional image is adjusted or a three-dimensional image is rotated, an unnecessary image is removed from each plane (e.g., Japanese Unexamined Patent Publication JP-A 2006-223712).

Now, a conventional method for displaying a three-dimensional image will be described with reference to FIGS. 1 and 2. FIGS. 1 and 2 are screen views for describing a conventional method for displaying a three-dimensional image included in a region of interest (ROI). Acquisition and display of a three-dimensional image of a fetus will be described here.

In the conventional method, by imaging a subject with an ultrasound probe, tomographic image data as two-dimensional image data is acquired at first. Then, as shown in FIG. 1, a tomographic image 100 is displayed on a display. The tomographic image 100 includes a fetus image 101. Then, before acquisition of three-dimensional image data, a region of interest (ROI) is set on the tomographic image 100.

For example, a marker 102 for designating a three-dimensional scan range and a marker 103 for designating a range to execute rendering and generate a three-dimensional image are displayed on the tomographic image 100. In the example shown in FIG. 1, the marker 102 has a fan-like shape for execution of convex scan. Moreover, the marker 103 indicating the range to execute rendering has a rectangular shape. The position and size of the marker 103 change in accordance with change of the position and shape of the marker 102. When the position and size of the marker 102 are arbitrarily changed by an operator, the position and size of the marker 103 are also changed in conjunction with the change of the marker 102.

When the marker 102 and the marker 103 are thus set on the tomographic image, a three-dimensional range designated with the marker 102 is scanned with ultrasound waves. Then, rendering is executed on, of data acquired in the scan, data within a range designated by the marker 103, and three-dimensional image data included in the range designated by the marker 103 is thereby generated.

In a case that the fetus image 101 is included in the range indicated by the marker 103 and no unnecessary image is included in the range indicated by the marker 103, a three-dimensional image of the fetus is displayed.

However, in the conventional method, it is difficult to appropriately display a three-dimensional image of the fetus because an image other than the fetus image 101 remains in the range indicated by the marker 103.

Therefore, in the conventional method, in order to remove the obstacle, by removing an image between a viewpoint and a region of interest (ROI) while rotating a three-dimensional image on a screen, a three-dimensional image included in the region of interest (ROI) is visualized.

For example, as shown in FIG. 2, a cut plane line 104 is set on the tomographic image 100 and, after an image between a viewpoint and the cut plane line 104 is removed, the remaining image is three-dimensionally displayed. This operation needs setting of the cut plane line 104 for each plane by rotating a three-dimensional image. Therefore, there is a need for setting the cut plane line from a certain view direction to remove an image and thereafter setting the cut plane line from another view direction to remove an image. Thus, there is a need for executing the abovementioned operation many times so that a three-dimensional image 105 representing a fetus shown in FIG. 2 is finally obtained.

DISCLOSURE OF THE INVENTION

Problem that the Invention is to Solve

When displaying the three-dimensional image 105 while displaying the tomographic image 100, it is demanded to display a three-dimensional image from which an unnecessary part is removed. However, the cut plane line should be repetitively set from all directions because it is impossible to cut other planes only by regulating the cut plane line. Thus, the operation is complicated, and it is impossible to display a desired three-dimensional image with a simple operation. Furthermore, there is a problem that, since a professional skill is required to repetitively operate the cut plane line to extract an object like a fetus, the object cannot be extracted with ease.

Besides, even when an image is removed by cube cut, an unnecessary part still remains. Therefore, it is necessary to remove the unnecessary part after displaying a three-dimensional image. Accordingly, in the conventional art, the operation is complicated, and it is difficult to extract a desired object with a simple operation. Therefore, it is difficult to extract a desired three-dimensional image (a three-dimensional image included in a region of interest) in a short time period.

The present invention has been made to solve the abovementioned problem, and an object of the present invention is to provide an ultrasound imaging apparatus capable of easily displaying a three-dimensional image included in a region of interest (ROI), and also provide a method for acquiring an ultrasound image.

Means for Solving the Problem

A first aspect of the present invention provides an ultrasound imaging apparatus, comprising: a scanner configured to transmit ultrasound waves to a subject and receive reflected waves from the subject; an image generator configured to generate tomographic image data based on the reflected waves; a marker generator configured to generate a first marker and a second marker; and a display controller configured to cause a display to display a tomographic image based on the tomographic image data and cause the display to display the first marker and the second marker so as to be superimposed on the tomographic image in a state that the second marker is included in a range of the first marker, wherein: the scanner executes scan with ultrasound waves on the range specified based on the first marker; and the image generator generates three-dimensional image data based on, of data acquired in the scan, data included in a range specified based on the second marker. Moreover, the marker generator generates a new second marker rotated in accordance with an instruction to rotate the second marker; the display controller causes the display to display the new second marker so as to be superimposed on the tomographic image; the scanner executes scan with ultrasound waves on the range specified based on the first marker; and the image generator generates three-dimensional image data based on, of data acquired in the scan, data included in a range specified based on the new second marker.

Further, a second aspect of the present invention provides a method for acquiring an ultrasound image, comprising: transmitting ultrasound waves to a subject and receiving reflected waves from the subject to generate tomographic image data based on the reflected waves; causing a display to display a tomographic image based on the tomographic image data and causing the display to display a first marker and a second marker so as to be superimposed on the tomographic image in a state that the second marker is included in a range of the first marker; executing scan with ultrasound waves on the range specified based on the first marker; and generating three-dimensional image data based on, of data acquired in the scan, data included in a range specified based on the second marker.

Moreover, a new second marker obtained by rotating in accordance with an instruction to rotate the second marker is generated and the new second marker is superimposed on the tomographic image and displayed on the display, and three-dimensional image data is generated based on, of the data acquired in the scan, data included in a range specified based on the new second marker.

Effect of the Invention

According to the present invention, by scanning a range specified by a first marker with ultrasound waves and generating three-dimensional image data based on data included in a range specified by a second marker, it is possible to remove an image unnecessary for diagnosis more easily than in the conventional art and obtain a three-dimensional image included in a region of interest.

Further, according to the present invention, since it is possible to rotate a second marker indicating a range to generate three-dimensional image data, it is possible to designate the range in accordance with the shape of an imaging object shown in a tomographic image. Consequently, it is possible to easily remove an image unnecessary for diagnosis and obtain a three-dimensional image included in a region of interest.

BEST MODE FOR CARRYING OUT THE INVENTION

First Embodiment (Configuration)

The configuration of an ultrasound imaging apparatus according to a first embodiment of the present invention will be described with reference to FIG. 3. FIG. 3 is a block diagram showing an ultrasound imaging apparatus according to the first embodiment of the present invention.

An ultrasound imaging apparatus 1 according to the first embodiment includes an ultrasound probe 2, a transceiver 3, a signal processor 4, a DSC 5, a first image memory 6, an image processor 7, a second image memory 8, a display controller 9, a display 10, an operation part 11, and a marker generator 12.

The ultrasound probe 2 is a two-dimensional array probe in which a plurality of ultrasound transducers are two-dimensionally arranged. The ultrasound probe 2 scans a three-dimensional range with ultrasound waves.

Moreover, the ultrasound probe 2 may be a one-dimensional array probe, which includes a plurality of ultrasound transducers aligned in a predetermined direction (a scan direction) and which can scan a three-dimensional range by mechanically oscillating the ultrasound transducers in a direction (an oscillation direction) orthogonal to the scan direction.

The transceiver 3 includes a transmitter and a receiver. The transceiver 3 supplies electric signals to the ultrasound probe 2 so that the ultrasound probe 2 generates ultrasound waves, and also receives echo signals received by the ultrasound probe 2.

The transmitter of the transceiver 3 includes a clock generation circuit, a transmission delay circuit and a pulsar circuit, which are not shown in the drawings. The clock generation circuit is a circuit that generates clock signals for determining the timing and frequency of transmission of ultrasound signals. The transmission delay circuit is a circuit that applies delay and executes transmission focus when ultrasound waves are transmitted. The pulsar circuit incorporates the same number of pulsars as individual paths (channels) corresponding to the respective transducers. The pulsar circuit generates drive pulses at delayed transmission timings, and supplies the drive pulses to the respective transducers of the ultrasound probe 2.

Further, the receiver of the transceiver 3 includes a preamplifier circuit, an A/D conversion circuit and a reception delay/adder circuit, which are not shown in the drawings. The preamplifier circuit amplifies an echo signal outputted from each of the transducers of the ultrasound probe 2 for each reception channel. The A/D conversion circuit executes A/D conversion on the amplified echo signals. The reception delay/adder circuit applies delay times necessary for determining the reception directionality to the echo signals after the A/D conversion, and adds the signals. By this addition, reflection components from directions corresponding to the reception directionality are enhanced. The signals added by the transceiver 3 will be referred to as "RF data (or raw data)."

The ultrasound probe 2 and the transceiver 3 correspond to an example of a "scanner" of the invention.

The signal processor 4 includes a B-mode processing circuit, a Doppler processing circuit and a color mode processing circuit. The RF data outputted from the transceiver 3 is processed in one of the processing circuits.

The B-mode processing circuit visualizes echo amplification information, and generates B-mode ultrasound raster data from echo signals. The Doppler processing circuit extracts Doppler shift frequency components and then executes an FFT process, etc., to generate data having blood-flow information. The color mode processing circuit visualizes moving blood-flow information to generate color ultrasound raster data. The blood-flow information includes information on velocity, dispersion, power, etc. The blood-flow information is obtained as binary information.

The DSC (Digital Scan Converter) 5 converts ultrasound raster data to image data represented by orthogonal coordinates in order to obtain an image represented by the orthogonal coordinate system. For example, the DSC 5 generates tomographic image data as two-dimensional information based on B-mode ultrasound raster data, and outputs the tomographic image data to the display controller 9. The display controller 9 causes the display 10 to display a tomographic image based on the tomographic image data. Moreover, the tomographic image data generated by the DSC 5 is stored into the first image memory 6. Besides, the raster data may be stored into the first image memory 6.

The image processor 7 reads a plurality of tomographic image data stored in the first image memory 6 to generate voxel data. Then, the image processor 7 executes image processing such as surface rendering, volume rendering and MPR (Multi Planner Reconstruction) on the voxel data, thereby generating ultrasound image data such as three-dimensional image data and image data in an arbitrary cross section (MPR image data). Moreover, the tomographic image data generated by the image processor 7 is stored into the second image memory 8.

The signal processor 4, the DSC 5, and the image processor 7 correspond to an example of an "image generator" of the present invention.

The display controller 9 causes the display 10 to display a tomographic image based on the tomographic image data outputted from the DSC 5, and an ultrasound image such as a three-dimensional image based on the three-dimensional image data outputted from the image processor 7.

Furthermore, the display controller 9 causes the display 10 to display a marker (a first marker) for designating a three-dimensional scan range (a first region of interest) and a marker (a second marker) for designating a range to generate ultrasound image data of a three-dimensional image, etc., so as to be superimposed on an ultrasound image such as a tomographic image.

Data included in the range specified based on the second marker (a second region of interest) is subjected to image processing such as rendering by the image processor 7.

The first and second markers are generated by the marker generator 12.

The marker generator 12 generates the first and second markers each surrounding a predetermined range. Coordinate information of the first marker generated by the marker generator 12 is outputted to the transceiver 3, the DSC 5 and the display controller 9, whereas coordinate information of the second marker is outputted to the image processor 7 and the display controller 9. Besides, the marker generator 12 generates a new second marker rotated in accordance with a rotating instruction from the operation part 11, and outputs coordinate information of the new second marker to the image processor 7 and the display controller 9.

Now, an example of setting a region of interest (ROI) will be described with reference to FIG. 4. FIG. 4 is a view of a screen for describing a region of interest (ROI) set in the ultrasound imaging apparatus according to the first embodiment of the invention. In this embodiment, acquisition and display of an image of a fetus will be described as an example.

First, the display controller 9 receives tomographic image data acquired in the scan with ultrasound waves from the DSC 5, and causes the display 10 to display a tomographic image based on the tomographic image data. For example, as shown in FIG. 4, the display controller 9 causes the display 10 to display a tomographic image 20 representing a fetus image 21.

The display controller 9 then causes the display 10 to display, in preset initial positions, a first marker 22 and a second marker 23 each having a predetermined size generated by the marker generator 12 so as to be superimposed on the tomographic image 20.

The range specified based on the first marker 22 represents a three-dimensional scan range (the first region of interest). Moreover, the range specified based on the second marker 23 represents a range to generate ultrasound image data such as three-dimensional image data (the second region of interest).

A three-dimensional range including a cross section indicated by the first marker 22 and having a predetermined range in a direction (a depth direction) substantially orthogonal to the cross section is the three-dimensional scan rage (the first region of interest) scanned with ultrasound waves. Moreover, a three-dimensional range including a cross section indicated by the second marker 23 and having a predetermined range in a direction substantially orthogonal to the cross section (a depth direction) is the range to generate ultrasound image data (the second region of interest).

In the example shown in FIG. 4, the marker generator 12 generates the first marker having a fan-like shape for execution of sector scan. The display controller 9 then causes the display 10 to display the first marker 22 having a fan-like shape. Moreover, the marker generator 12 generates the second marker having a rectangular shape. The display controller 9 then causes the display 10 to display the second marker 23 having a rectangular shape. At this moment, the display controller 9 causes the display 10 to display the first marker 22 and the second marker 23 so that the second marker 23 is included in the range of the first marker 22.

The operator can move the first marker 22 and the second marker 23 on the display 10 and change the sizes thereof by the operation part 11. Upon reception of an instruction to move or rotate the markers from the operation part 11, in accordance with the instruction, the marker generator 12 generates new first and second markers and outputs them to the display controller 9, etc.

Upon reception of coordinate information of the new first and second markers from the marker generator 12, the display controller 9 causes the display 10 to display the new first and second markers.

When the operator gives an instruction to move the second marker 23 in the vertical or horizontal direction by using the operation part, the marker generator 12 generates a new second marker in accordance with the instruction. The display controller 9 then causes the display 10 to display the new second marker 23. Moreover, when the operator gives an instruction to rotate the second marker 23 by the operation part 11, the marker generator 12 generates a new second marker obtained by rotating around a predetermined rotation axis in accordance with the instruction. The display controller 9 then causes the display 10 to display the new second marker 23. For example, in the case of acquiring a three-dimensional image with a fetus as a region of interest, the operator moves or rotates the second marker 23 by using the operation part 11 so that the fetus is included in the range surrounded by the second marker 23.

The second marker 23 may be movable on the orthogonal coordinate system, or may be movable on the polar coordinate system. Moreover, the second marker may have a shape other than the rectangular shape, and may have a curved shape. For example, the marker generator 12 may generate the second marker 23 having an arbitrary shape such as a circular shape and an elliptic shape.

When the three-dimensional scan range (the first region of interest) is designated with the first marker 22 and the range to generate three-dimensional image data (the second region of interest) is designated with the second marker 23 as described above, the coordinate information of the first marker 22 is outputted from the marker generator 12 to the transceiver 3 and the DSC 5, and the coordinate information of the second marker 23 is outputted from the marker generator 12 to the image processor 7.

Upon reception of the coordinate information of the first marker 22 from the marker generator 12, the transceiver 3 causes the ultrasound probe 2 to scan the three-dimensional scan range specified based on the first marker 22. That is, the transceiver 3 causes the ultrasound probe 2 to scan the three-dimensional scan range including the cross section indicated by the first marker 22 and having the predetermined range in the direction substantially orthogonal to the cross section (the depth direction). For example, the transceiver 3 transmits ultrasound waves to various depths by changing the repetition frequency (PRF) of the ultrasound waves, and transmits the ultrasound waves while changing the deflection direction. Signals acquired in this scan are processed by the signal processor 4 and the DSC 5, and a plurality of tomographic image data are thereby generated. The plurality of tomographic image data are stored into the first image memory 6.

The image processor 7 reads the plurality of tomographic image data from the first image memory 6 and generates voxel data. Then, the image processor 7 receives the coordinate information of the second marker 23 from the marker generator 12 and executes image processing such as volume rendering on data included in the three-dimensional range specified based on the second marker 23, thereby generating ultrasound image data such as three-dimensional image data. That is, the image processor 7 executes image processing such as volume rendering on data included in the three-dimensional range including the cross section indicated by the second marker 23 and having the predetermined range in the direction substantially orthogonal to the cross section (the depth direction), thereby generating ultrasound image data such as three-dimensional image data. These generated ultrasound image data like three-dimensional image data are stored into the second image memory 8.

The display controller 9 then reads the three-dimensional image data from the second memory 8 and causes the display 10 to display a three-dimensional image based on the three-dimensional image data. This three-dimensional image represents an image included in the three-dimensional range specified based on the second marker 23. By adjusting the position, size and rotation angle of the second marker 23 so that the fetus is included within the second marker 23 as in the example of FIG. 4, it is possible to obtain a three-dimensional image from which an unnecessary part is deleted.

The operation part 11 is composed of a keyboard, a mouse, a trackball, a TCS (Touch Command Screen), or the like. Through an operation of the operation part 11 by the operator, a scan condition, a region of interest (ROI), etc. are set. The display 10 may be a monitor such as a CRT and a liquid crystal display. A tomographic image, a three-dimensional image, blood-flow information, etc., are displayed on a screen of the display 10.

The image processor 7 includes a CPU, GPU, ASIC or FPGA, and a storage device such as a ROM, RAM and HDD. The storage device stores a three-dimensional image data generation program. Through execution of the three-dimensional image data generation program by the CPU, volume rendering is executed on the data included in the three-dimensional range specified with the second marker, and three-dimensional image data is thereby generated.

Further, the display controller 9 includes a CPU and a storage device such as a ROM, RAM and HDD. The storage device stores a display control program. Through execution of the display control program by the CPU, a tomographic image is displayed on the display 10, and moreover, the first marker for designating the first region of interest and the second marker for designating the second region of interest are displayed on the display 10 so as to be superimposed on the tomographic image. Besides, when the three-dimensional image data is generated, a three-dimensional image based on the three-dimensional image data is displayed on the display 10 through execution of the display control program by the CPU.

Further, the marker generator 12 includes a CPU and a storage device such as a ROM, RAM and HDD. The storage device stores a marker generation program. Through execution of the marker generation program by the CPU, the marker generator 12 generates the first and second markers, receives an instruction to rotate or move from the operation part 11, and generates new first and second markers in accordance with the instruction.

(Operation)

Next, the operation of the ultrasound imaging apparatus 1 according to the first embodiment of the present invention will be described with reference to FIG. 5. FIG. 5 is a flow chart showing a series of operations by the ultrasound imaging apparatus according to the first embodiment of the present invention.

(Step S01)

First, the ultrasound probe 2 is caused to scan a subject with ultrasound waves, and tomographic image data as two-dimensional image data is thereby acquired. Then, the display controller 9 causes the display 10 to display the tomographic image data. For example, as shown in FIG. 4, the display controller 9 causes the display 10 to display the tomographic image 20 including the fetus image 21.

(Step S02)

Next, the display controller 9 causes the display 10 to display, in preset initial positions, the first and second markers 22 and 23 each having a predetermined size generated by the marker generator 12 so as to be superimposed on the tomographic image 20.

(Step S03)

By using the operation part 11 while referring to the first and second markers 22 and 23 displayed on the display 10, the operator gives an instruction to move the first and second markers 22 and 23 to desired positions. The marker generator 12 generates new first and second markers 22 and 23 in accordance with the moving instruction. Then, the display controller 9 causes the display 10 to display the new first and second markers 22 and 23. Moreover, by using the operation part 11, the operator gives an instruction to rotate the second marker 23 in accordance with the skew of a fetus image so that the fetus image is included. The marker generator 12 generates a second marker rotated in accordance with the rotating instruction, and the display controller 9 causes the display 10 to display the new second marker. Thus, the three-dimensional scan range (the first region of interest) is designated with the first marker 22, and the range to generate three-dimensional image data (the second region of interest) is designated with the second marker 23. The coordinate information of the first marker 22 is outputted from the marker generator 12 to the transceiver 3 and the DSC 5, and the coordinate information of the second marker 23 is outputted from the marker generator 12 to the image processor 7. It should be noted that the first marker 22 and the second marker 23 can be separately rotated, moved and regulated in size.

(Step S04)

Upon reception of the coordinate information of the first marker 22 from the marker generator 12, the transceiver 3 causes the ultrasound probe 2 to scan the three-dimensional scan range specified based on the first marker 22. That is, the transceiver 3 causes the ultrasound probe 2 to scan the three-dimensional scan range including the cross section indicated by the first marker 22 and having the predetermined range in the direction substantially orthogonal to the cross section (the depth direction).

(Step S05)

After the three-dimensional scan range is scanned in step S04, the signal processor 4 and the DSC 5 execute predetermined processes on signals acquired in the scan, and a plurality of tomographic image data are thereby generated.

(Step S06)

The image processor 7 then generates voxel data based on the plurality of tomographic image data generated by the DSC 5. Moreover, the image processor 7 executes volume rendering on the voxel data to generate three-dimensional image data. Since having received the coordinate information of the second marker 23 from the marker generator 12, the image processor 7 executes volume rendering on data included in the three-dimensional range (the second region of interest) specified based on the second marker 23, thereby generating three-dimensional image data included in the second region of interest. That is, the image processor 7 generates the three-dimensional image data by executing volume rendering on data included in the three-dimensional range including the cross section indicated by the second marker 23 and having the predetermined range in the direction substantially orthogonal to the cross section (the depth direction).

(Step S07)

Upon reception of the three-dimensional image data generated by the image processor 7, the display controller 9 causes the display 10 to display a three-dimensional image based on the three-dimensional image data.

As described above, the ultrasound imaging apparatus 1 according to the first embodiment allows the second marker 23 for designating a range in which three-dimensional image data is generated to rotate around a predetermined rotation axis, and therefore, has an effect that it is easy to match a region of interest with the morphology of an observation object (the morphology of a fetus in the example of FIG. 4). Consequently, it is possible to obtain a three-dimensional image with less unnecessary part than conventional and to display the image on the display 10. Thus, the ultrasound imaging apparatus 1 according to the first embodiment makes it possible to easily display a three-dimensional image included in a region of interest without a complicated operation.

Second Embodiment

Next, an ultrasound imaging apparatus according to a second embodiment of the present invention will be described with reference to FIGS. 6A through 6C. FIGS. 6A through 6C are schematic views for describing a process of obtaining a new three-dimensional scan range in the ultrasound imaging apparatus according to the second embodiment of the present invention.

Similarly to the ultrasound imaging apparatus 1 according to the first embodiment described above, the ultrasound imaging apparatus according to the second embodiment includes the ultrasound probe 2, the transceiver 3, the signal processor 4, the DSC 5, the first image memory 6, the image processor 7, the second image memory 8, the display controller 9, the display 10, the operation part 11, and the marker generator 12. The second embodiment is featured by the content of the processing by the marker generator 12.

Upon reception of an instruction to change the position, size and rotation angle of the second marker for designating the range in which ultrasound image data (the second region of interest) is generated from the operation part 11, the marker generator 12 generates a new first marker with the position and size changed in accordance with the change of the second marker. The marker generator 12 obtains the position and size of the new first marker based on the coordinate information of the second marker after the change of the position, size and rotation angle.

The marker generator 12 generates a new first marker including a range designated by the second marker (the second region of interest). For example, the marker generator 12 obtains the new position and size of the first marker so that the range designated by the second marker (the second region of interest) is inscribed. At this moment, the marker generator 12 may inscribe the second region of interest to the first region of interest, or may reduce the size of the first region of interest by a predetermined size.

For example, as shown in FIG. 6A, the display controller 9 causes the display 10 to display the first marker 22 for designating the three-dimensional scan range (the first region of interest) and the second marker 23 for designating the three-dimensional image generation range (the second region of interest) in the initial state. Consequently, the three-dimensional scan range (the first region of interest) and the three-dimensional image generation range (the second region of interest) are designated. Then, when given an instruction to rotate and contract the second marker by the operation part 11, the marker generator 12 generates a new second marker rotated and contracted in accordance with the instruction. The display controller 9 causes the display 10 to display a new second marker 23a rotated and contracted as shown in FIG. 6B. The coordinate information of the new second marker 23a is outputted to the image processor 7.

Based on the coordinate information (the coordinate information of the respective apexes) of the new second marker 23a, the marker generator 12 obtains the coordinates of apexes α and β of the second marker 23a with which boundaries A and B first intersect. The boundaries A and B are boundaries of the first region of interest and are along the transmission/reception direction of ultrasound waves. Then, the marker generator 12 sets the boundaries A and B contacting the apexes α and β of the second marker 23a as the boundaries of the new first region of interest, and sets a range defined by the boundaries A and B as the new first region of interest (a range indicated by the first marker). In FIG. 6C, a range surrounded by the first marker 22a is the new first region of interest. For obtaining an image symmetric about the center of the ultrasound probe 2, the coordinates that the boundary A or B first intersects are obtained. Thus, the marker generator 12 generates the new first marker 22a whose width in a direction (a scan direction) substantially orthogonal to the transmission/reception direction of ultrasound waves has been changed in accordance with the new second marker 23a. That is, in accordance with the shape of the new second marker 23a, the marker generator 12 changes a scan range in the direction (the scan direction) substantially orthogonal to the transmission/reception direction of ultrasound waves.

In the example shown in FIGS. 6A, 6B and 6C, the second markers 23 and 23a have rectangular shapes. In this case, of the four apexes of the second marker 23a, the two apexes α and β located shallow in depth in the transmission/reception direction are apexes with which the boundaries A and B first intersect. Therefore, the marker generator 12 may set the boundaries A and B intersecting with the two apexes α and β located shallow in depth as the boundaries of the new first region of interest, and set the range defined by the boundaries A and B as the new first region of interest (the range indicated by the first marker).

Further, instead of making the boundaries A and B intersect with the apexes α and β of the second marker 23a, the marker generator 12 may displace the boundaries A and B from the intersecting points α and β by predetermined distances and set a range defined by the displaced boundaries A and B as the new first region of interest (the range indicated by the first marker). In the example shown in FIG. 6C, the marker generator 12 displaces the boundaries A and B toward the inside of the second marker 23a by predetermined distances, and sets the range defined by the displaced boundaries A and B as the new first region of interest (the range indicated by the first marker 22a).

The marker generator 12 outputs the coordinate information of the new first region of interest (the first marker) to the transceiver 3, the DSC 5 and the display controller 9. The display controller 9 causes the display 10 to display the first marker 22a indicating the new first region of interest and the second marker 23a so as to be superimposed on a tomographic image. The transceiver 3 causes the ultrasound probe 2 to scan the new first region of interest.

The above process is particularly effective for reducing the size of the second marker. A range that is not included in the range designated by the second marker (the second region of interest) is not an object for image processing by the image processor 7. Therefore, a range that is included in the first region of interest but not included in the second region of interest will not be used for generation of a three-dimensional image even if it is scanned with ultrasound waves. Accordingly, in the case of reducing the size of the second marker, it is possible, by making the three-dimensional scan range (the first region of interest) narrow in accordance with the reduction of the size, to increase the frame rate (volume rate).

(Operation)

Next, the operation of the ultrasound imaging apparatus according to the second embodiment of the present invention will be described with reference to FIG. 7. FIG. 7 is a flow chart showing a series of operations by the ultrasound imaging apparatus according to the second embodiment of the present invention.

(Step S10)

First, as shown in FIG. 6A, the display controller 9 causes the display 10 to display, in preset initial positions, the first and second markers 22 and 23 generated by the marker generator 12 and having predetermined sizes so as to be superimposed on a tomographic image (not shown).

(Step S11)

By using the operation part 11 while referring to the first and second markers 22 and 23 displayed on the display 10, the operator gives an instruction to change the size, position and rotation angle of the second marker 23 as shown in FIG. 6B. Here, the second marker 23 is reduced in size and rotated. Upon reception of the changing instruction from the operation part 11, the marker generator 12 generates a new second marker in accordance with the instruction. Then, the display controller 9 causes the display 10 to display the new second marker 23a. The coordinate information of the second marker 23a is also outputted to the image processor 7 from the marker generator 12.

(Step S12)

The marker generator 12 sets the boundaries A and B intersecting with the two apexes α and β shallow in depth in the transmission/reception direction of the apexes of the second marker 23a, as the boundaries of a new first region of interest. The marker generator 12 then sets a range defined by the boundaries A and B as a new first region of interest (the first marker).

Thus, the marker generator 12 generates a new first marker 22a whose width in a direction (the scan direction) substantially orthogonal to the transmission/reception direction of ultrasound waves have been changed, based on the new second marker 23a.

(Step S13)

The coordinate information of the new first region of interest is outputted from the marker generator 12 to the transceiver 3, the DSC 5 and the display controller 9.

(Step S14)

Upon reception of the coordinate information of the new first region of interest (the first marker) from the marker generator 12, the display controller 9 causes the display 10 to display the first marker 22a indicating the new first region of interest and the second marker 23a so as to be superimposed on a tomographic image (not shown) (refer to FIG. 6C).

(Step S15)

Upon reception of the coordinate information of the new first region of interest from the marker generator 12, the transceiver 3 causes the ultrasound probe 2 to scan the first region of interest. For example, the transceiver 3 transmits ultrasound waves to various depths by changing the repetition frequency (PRF) of the ultrasound waves, and transmits the ultrasound waves while changing the deflection direction. That is, the transceiver 3 causes the ultrasound probe 2 to scan a three-dimensional scan range that includes a cross section indicated by the first marker 22a and that has a predetermined range in a direction (a depth direction) substantially orthogonal to the cross section.

(Step S16)

After the three-dimensional scan range is scanned in step S16, the signal processor 4 and the DSC 5 execute predetermined processes on signals acquired in the scan, and a plurality of tomographic image data are thereby generated.

(Step S17)

The image processor 7 then generates voxel data based on the plurality of tomographic image data generated by the DSC 5. Moreover, the image processor 7 executes volume rendering on the voxel data to generate three-dimensional image data. Since having received the coordinate information of the second marker 23a from the marker generator 12, the image processor 7 executes volume rendering on data included in the three-dimensional range (the second region of interest) specified based on the second marker 23a, thereby generating three-dimensional image data included in the second region of interest. That is, the image processor 7 generates three-dimensional image data by executing volume rendering on data included in a three-dimensional range that includes a cross section indicated by the second marker 23a and that has a predetermined range in a direction (a depth direction) substantially orthogonal to the cross section.

(Step S18)

Upon reception of the three-dimensional image data generated by the image processor 7, the display controller 9 causes the display 10 to display a three-dimensional image based on the three-dimensional image data.

As described above, the ultrasound imaging apparatus according to the second embodiment can produce the same actions and effects as the ultrasound imaging apparatus 1 according to the first embodiment described above. Moreover, the change of the position and size of the three-dimensional scan range (the first region of interest) in accordance with the change of the size and position of the second marker 23 avoids scanning an unnecessary part. Accordingly, it is possible to increase the frame rate (the volume rate).

In particular, in the case of reducing the size of the second region of interest, it is possible to avoid scanning an unnecessary part and thereby increase the frame rate (the volume rate).

Further, the marker generator 12 may generate the first marker with the width (the depth) in the transmission/reception direction of ultrasound waves changed based on the new marker 23a. That is, the marker generator 12 may change the depth of transmission of ultrasound waves in accordance with the shape of the new second marker 23a. Here, a process for generating the first marker whose width (depth) in the transmission/reception direction of ultrasound waves is changed will be described with reference to FIG. 8. FIG. 8 is a schematic view for describing a process for obtaining a new three-dimensional scan range in the ultrasound imaging apparatus according to the second embodiment of the present invention.

For example, as shown in FIG. 8, the marker generator 12 sets a boundary C located in the deepest position of the boundaries of the new first region of interest along a direction (a scan direction) substantially orthogonal to the transmission/reception direction, near an apex γ in the deepest position in the transmission/reception direction of all the apexes of the second marker 23a, based on the coordinate information (the coordinate information of the respective apexes) of the new second marker 23a. That is, the marker generator 12 sets the boundary C of the first region of interest, near the deepest part (the apex γ) of the second marker 23a. This boundary C defines the depth of the new first region of interest. Then, the marker generator 12 sets a range defined by the boundaries A, B and C as the new first region of interest (the range indicated by the first marker). In FIG. 8, the range surrounded by the first marker 22a becomes the new first region of interest defined by the board lines A, B and C.

As described above, by changing the position of the boundary C forming the first region of interest (the range surrounded by the first marker 22a) in accordance with the shape of the new second marker 23a, it is possible to make the second region of interest indicating an image generation range included in the first region of interest scanned with the ultrasound waves.

Further, as shown in FIG. 8, the marker generator 12 may set a boundary C1 of the first marker 22a between the two apexes γ and δ located in the deepest positions in the transmission/reception direction of the four apexes of the second marker 23a. In this case, the marker generator 12 sets a range defined by the boundaries A, B and C1 as the new first region of interest. Furthermore, the marker generator 12 may set the boundary C in the vicinity of the apex δ of the second marker 23a.

The marker generator 12 outputs the coordinate information of the new first region of interest (the first marker) to the transceiver 3, the DSC 5 and the display controller 9. The display controller 9 causes the display 10 to display the first marker 22a indicating the new first region of interest and the second marker 23a so as to be superimposed on a tomographic image. The transceiver 3 causes the ultrasound probe 2 to scan the new first region of interest. At this moment, the transceiver 3 transmits and receives ultrasound waves while changing the repetition frequency (PRF) of the ultrasound waves in accordance with the depth in the transmission/reception direction defined by the boundary C of the first region of interest. Then, the image processor 7 executes volume rendering on data included in a three-dimensional range specified based on the second marker 23a, thereby generating three-dimensional image data included in the second region of interest.

Third Embodiment

Next, the configuration of an ultrasound imaging apparatus according to a third embodiment of the present invention will be described with reference to FIGS. 9A through 9E. FIGS. 9A through 9E are schematic views for describing a process of obtaining a new region of interest (ROI) in the ultrasound imaging apparatus according to the third embodiment of the present invention.

Similarly to the ultrasound imaging apparatus according to the first embodiment described above, the ultrasound imaging apparatus according to the third embodiment includes the ultrasound probe 2, the transceiver 3, the signal processor 4, the DSC 5, the first image memory 6, the image processor 7, the second image memory 8, the display controller 9, the display 10, the operation part 11 and the marker generator 12. The third embodiment is featured by the content of processing by the marker generator 12.

In a case that the position and size of a second marker for designating a range to generate ultrasound image data (a second region of interest) are changed and thereafter the position and size of a first marker for designating a three-dimensional scan range (a first region of interest) are changed, the marker generator 12 generates a new second marker with the position and size changed in accordance with the change of the first marker. The marker generator 12 obtains the position and size of the new second marker based on the coordinate information of the first marker whose position and size have been changed.

When the second marker is rotated θ degrees to be displaced and thereafter the position and size of the first marker are changed, the marker generator 12, in accordance with the size of the first marker, changes the size of the second region of interest of the initial state designated by the second marker before rotated. At this moment, the marker generator 12 changes the size of the second marker at the same rate as the change rate of the size of the first marker. Then, the marker generator 12 makes the second region of interest changed in size also rotate θ degrees in the same direction as the second marker has been rotated, and sets as the new second region of interest (the range indicated by the second marker).

A specific process will be described with reference to FIGS. 9A through 9E. As shown in FIG. 9A, in the initial state, the display controller 9 causes the display 10 to display the first marker 22 for designating the three-dimensional scan range (the first region of interest) and the second marker 23 for designating the three-dimensional image generation range (the second region of interest). Thus, the three-dimensional scan range (the first region of interest) and the three-dimensional image generation range (the second region of interest) are designated.

When given an instruction to rotate the second marker by the operation part 11, the marker generator 12 rotates the second marker θ degrees in accordance with the instruction to generate a new one. As shown in FIG. 9B, the display controller 9 then causes the display 10 to display a new second marker 23b having been rotated. Moreover, when given an instruction to enlarge the first marker 22 of the initial state by the operation part 11, the marker generator 12 enlarges the first marker in accordance with the instruction to generate a new one. The display controller 9 then causes the display 10 to display a new first marker 22b having been enlarged as shown in FIG. 9C.

The marker generator 12 changes the size of the second marker 23 of the initial state in accordance with the size of the first marker 22b based on the coordinate information of the new first marker 22b and sets as a new second region of interest. This new second region of interest corresponds to a range indicated by a second marker 23c in FIG. 9D. The marker generator 12 makes the new second region of interest (the range indicated by the second marker 23c) rotate θ degrees and sets as a new second region of interest. This new second region of interest corresponds to a range indicated by a second marker 23d in FIG. 9E.

The marker generator 12 outputs the coordinate information of the changed first region of interest (the range indicated by the first marker 22b) to the transceiver 3 and the DSC 5, and outputs the coordinate information of the new second region of interest (the range indicated by the second marker 23d) to the image processor 7 and the display controller 9. The display controller 9 causes the display 10 to display the first marker and the second marker indicating the new second region of interest so as to be superimposed on a tomographic image. For example, as shown in FIG. 9E, the display controller 9 causes the display 10 to display the changed first marker 22b and the changed second marker 23d so as to be superimposed on a tomographic image (not shown). The transceiver 3 causes the ultrasound probe 2 to scan the first region of interest.

The above process is particularly effective for scanning a range that is out of the second marker after the second marker is moved and rotated. In this case, by broadening and moving the first marker after moving and rotating the second marker, a desired scan range is designated. Then, by changing the size of the second region of interest in accordance with the change of the first marker, it is possible to easily set a desired region of interest without a complicated operation.

(Operation)

Next, the operation of the ultrasound imaging apparatus according to the third embodiment of the present invention will be described with reference to FIG. 10. FIG. 10 is a flow chart showing a series of operations by the ultrasound imaging apparatus according to the third embodiment of the present invention.

(Step S20)

First, as shown in FIG. 9A, the display controller 9 causes the display 10 to display, in preset initial positions, the first and second markers 22 and 23 having predetermined sizes generated by the marker generator 12 so as to be superimposed on a tomographic image (not shown).

(Step S21)

By using the operation part 11 while referring to the first and second markers 22 and 23 displayed on the display 10, the operator gives an instruction to change the size, position and rotation angle of the second marker 23 as shown in FIG. 9B. Here, the second marker 23 is rotated. Upon reception of the changing instruction from the operation part 11, the marker generator 12 generates a second marker rotated θ degrees in accordance with the instruction. Then, the display controller 9 causes the display 10 to display the new second marker 23b.

(Step S22)

Furthermore, by using the operation part 11 while referring to the first marker 22 displayed on the display 10, the operator gives an instruction to change the size of the first marker 22 as shown in FIG. 9C. Upon reception of the changing instruction from the operation part 11, the marker generator 12 generates the first marker 22b with the enlarged range in accordance with the instruction. Then, the display controller 9 causes the display 10 to display the new first marker 22b.

(Step S23)

The marker generator 12 temporarily changes the size of the second region of interest (the range designated by the second marker 23) set in the initial state in accordance with the change of the size of the first marker, and sets as a new second region of interest. This new second region of interest corresponds to a range indicated by the second marker 23c in FIG. 9D.

(Step S24)

Then, the marker generator 12 makes the second region of interest with the changed size (the range designated by the second marker 23c) rotate θ degrees, and sets as a new second region of interest. This new second region of interest corresponds to a range indicated by the second marker 23d in FIG. 9E.

(Step S25)

The coordinate information of the changed first region of interest (the range indicated by the first marker 22b) is outputted to the transceiver 3 and the DSC 5 from the marker generator 12. Moreover, the coordinate information of the new second region of interest (the range indicated by the second marker 23d) is outputted to the image processor 7 and the display controller 9.

(Step S26)

Upon reception of the coordinate information of the new second region of interest (the range indicated by the second marker 23d) from the marker generator 12, the display controller 9 causes the display 10 to display the first marker and the second marker indicating the new second region of interest. For example, as shown in FIG. 9E, the display controller 9 causes the display 10 to display the changed first marker 22b and the changed second marker 23d so as to be superimposed on a tomographic image (not shown).

(Step S27)

Upon reception of the coordinate information of the first region of interest (the first marker 22b) from the marker generator 12, the transceiver 3 causes the ultrasound probe 2 to scan the first region of interest. That is, the transceiver 3 causes the ultrasound probe 2 to scan a three-dimensional scan range that includes a cross section indicated by the first marker 22b and that has a predetermined range in a direction (a depth direction) substantially orthogonal to the cross section.

(Step S28)

After the three-dimensional scan range is scanned in step S27, the signal processor 4 and the DSC 5 execute predetermined processes on signals acquired in the scan, and a plurality of tomographic image data are thereby generated.

(Step S29)

The image processor 7 then generates voxel data based on the plurality of tomographic image data generated by the DSC 5. Moreover, the image processor 7 executes volume rendering on the voxel data, thereby generating three-dimensional image data. Since having received the coordinate information of the second region of interest specified by the second marker 23d from the marker generator 12, the image processor 7 executes volume rendering on data included in the second region of interest, thereby generating three-dimensional image data included in the second region of interest. That is, the image processor 7 generates three-dimensional image data by executing volume rendering on data included in a three-dimensional range that includes a cross section indicated by the second marker 23d and that has a predetermined range in a direction (a depth direction) substantially orthogonal to the cross section.

(Step S30)

Upon reception of the three-dimensional image data generated by the image processor 7, the display controller 9 causes the display 10 to display a three-dimensional image based on the three-dimensional image data.

As described above, the ultrasound imaging apparatus according to the third embodiment can produce the same actions and effects as the ultrasound imaging apparatus 1 according to the first embodiment described above.

Moreover, by changing the position and size of the second region of interest in accordance with the change of the size and position of the first marker 22, it is possible to set a desired region of interest by a simple operation without a complicated operation.

Figure 1:
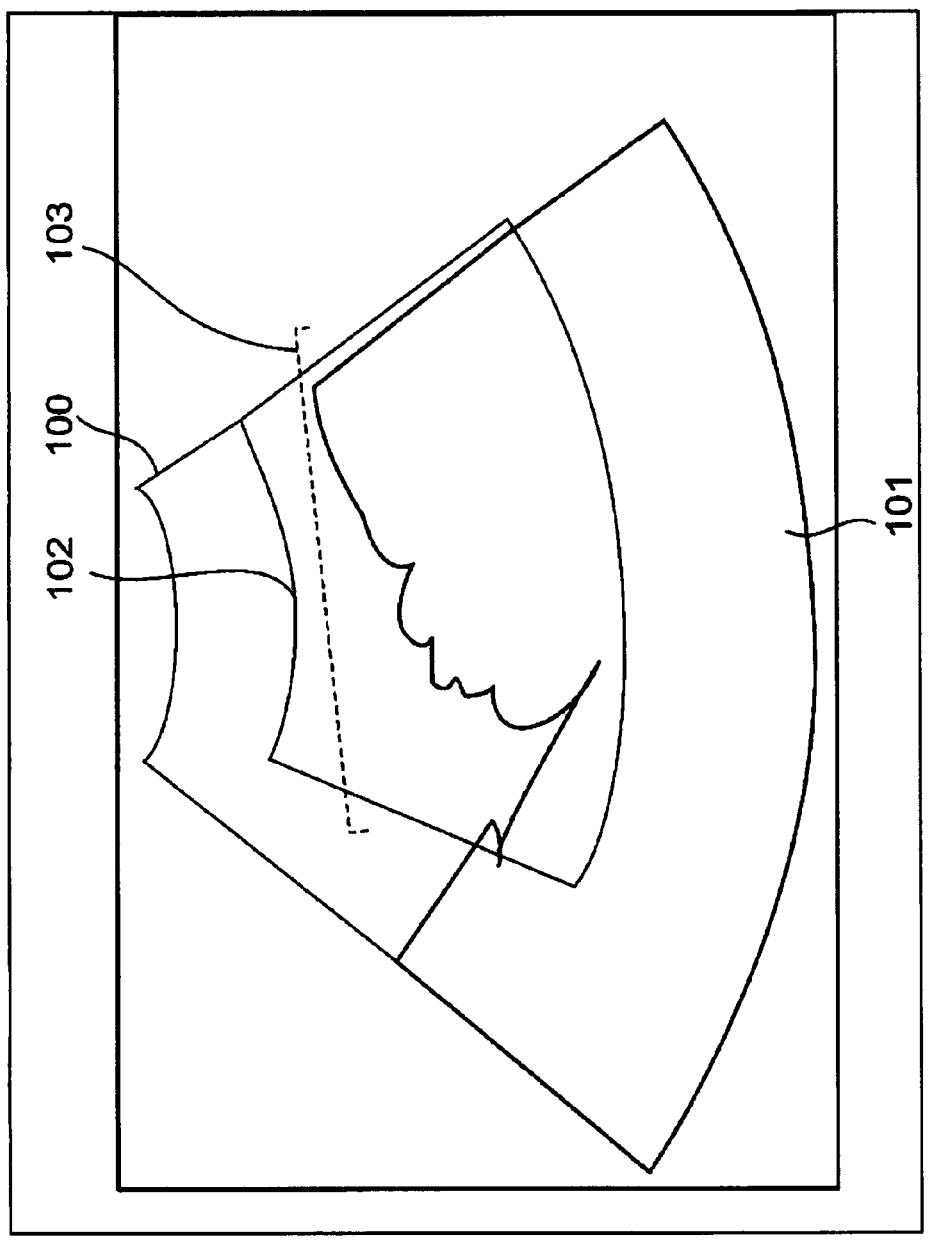
FIG. 1 is a view for describing a method for displaying a three-dimensional image included in a region of interest (ROI) in a conventional art.
Figure 2:
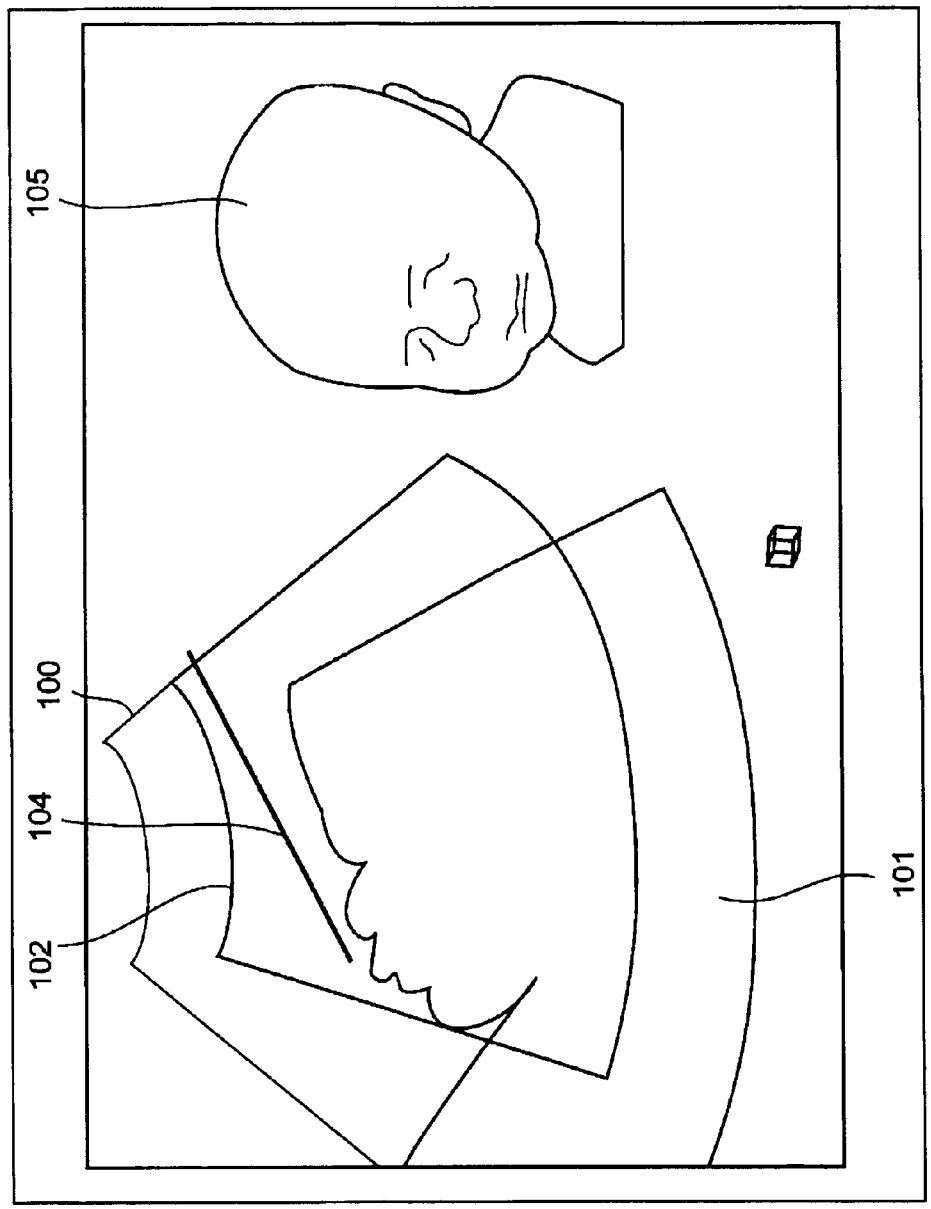
FIG. 2 is a view for describing a method for displaying a three-dimensional image included in a region of interest (ROI) in a conventional art.
Figure 3:
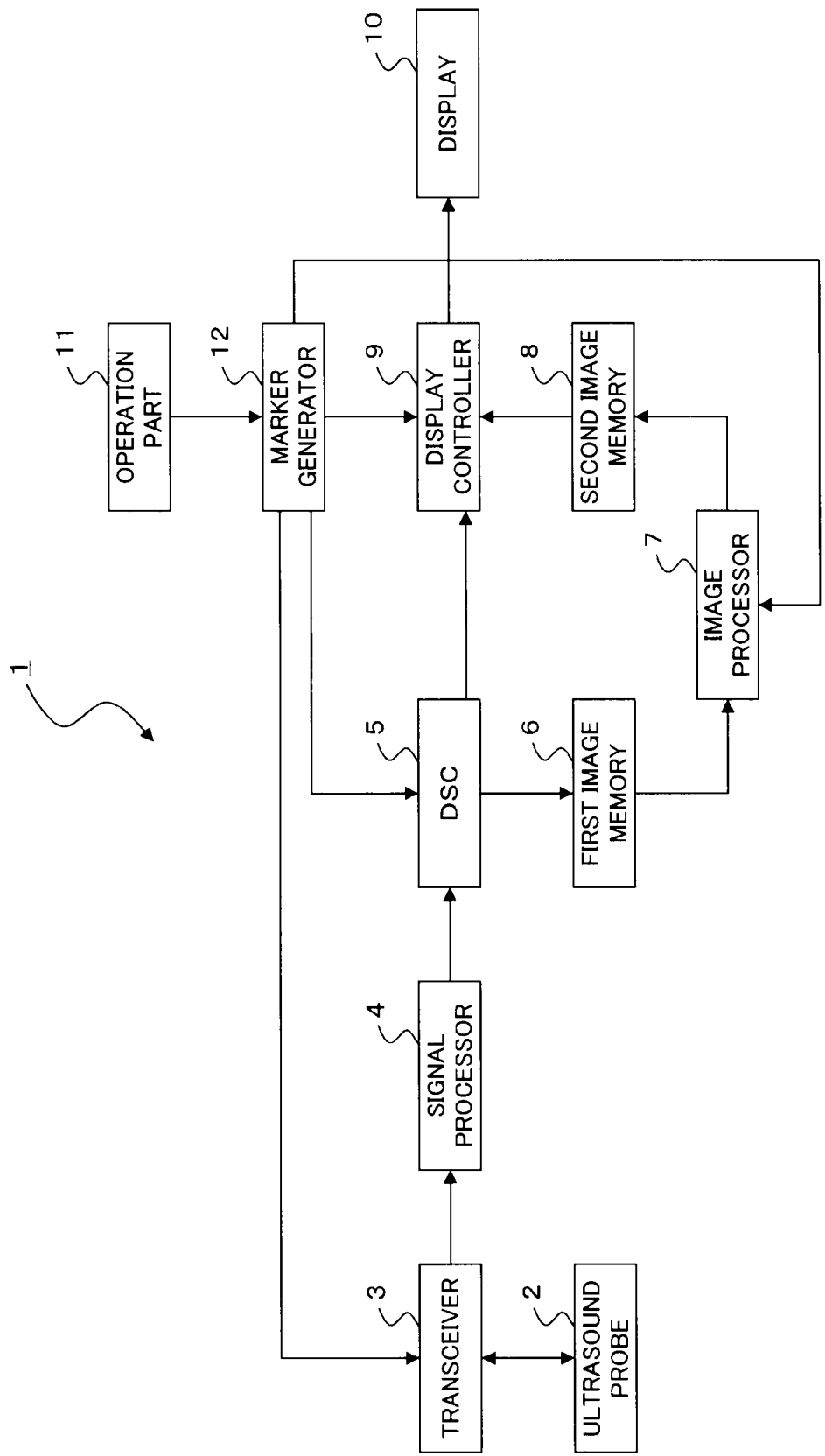
FIG. 3 is a block diagram showing an ultrasound imaging apparatus according to a first embodiment of the present invention.
Figure 4:
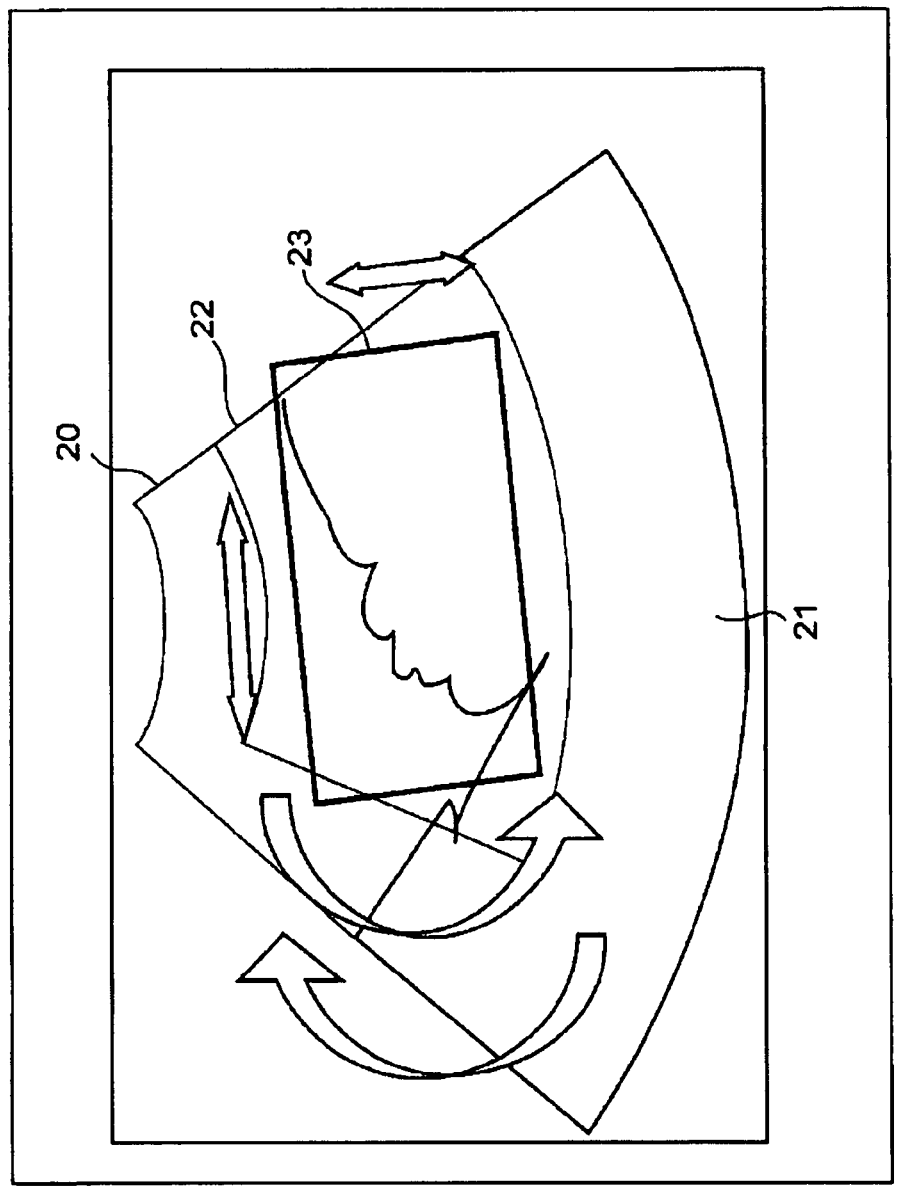
FIG. 4 is a view of a screen for describing a region of interest (ROI) set in the ultrasound imaging apparatus according to the first embodiment of the present invention.
Figure 5:
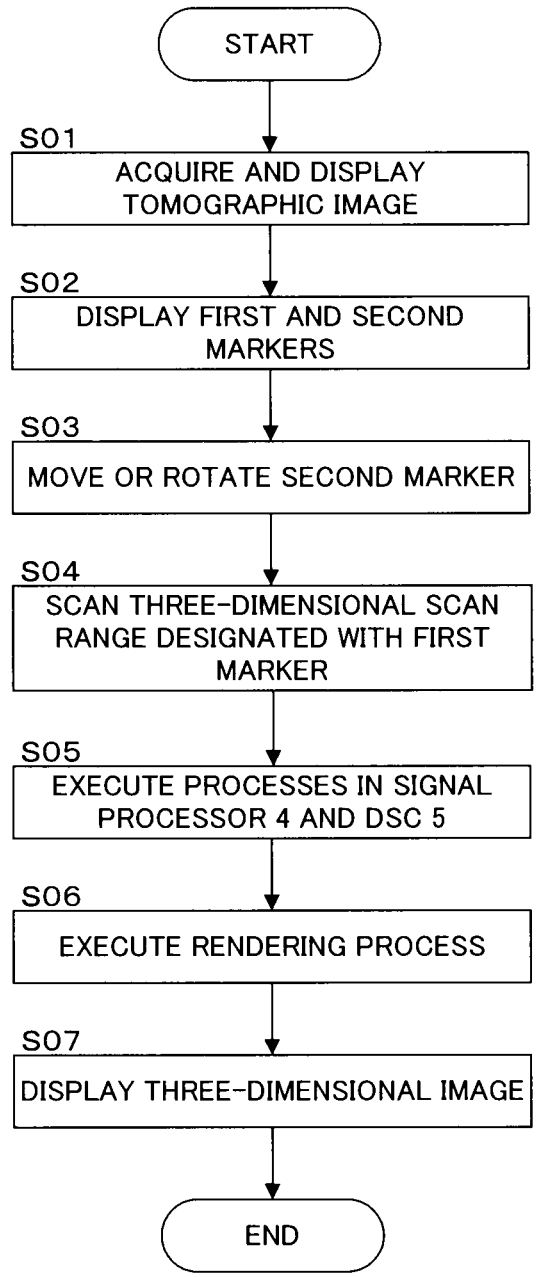
FIG. 5 is a flow chart showing a series of operations by the ultrasound imaging apparatus according to the first embodiment of the present invention.
Figure 6A:
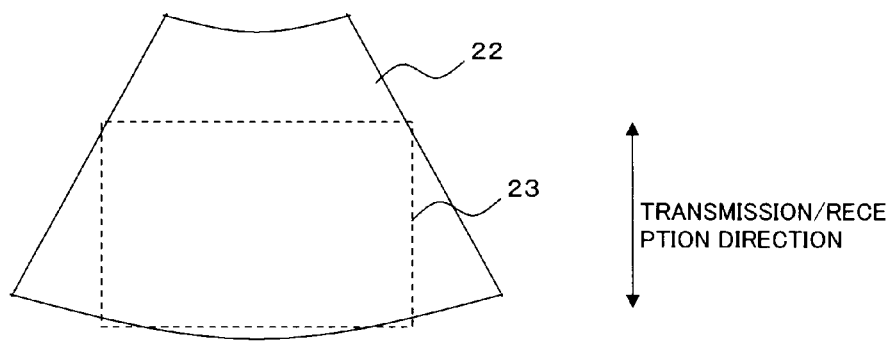
FIGS. 6A through 6C are schematic views for describing a process of obtaining a new three-dimensional scan range in an ultrasound imaging apparatus according to a second embodiment of the present invention.
Figure 6B:
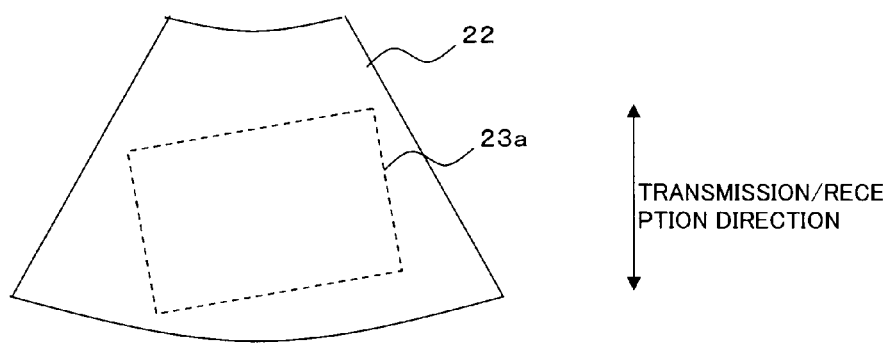
Figure 6C:
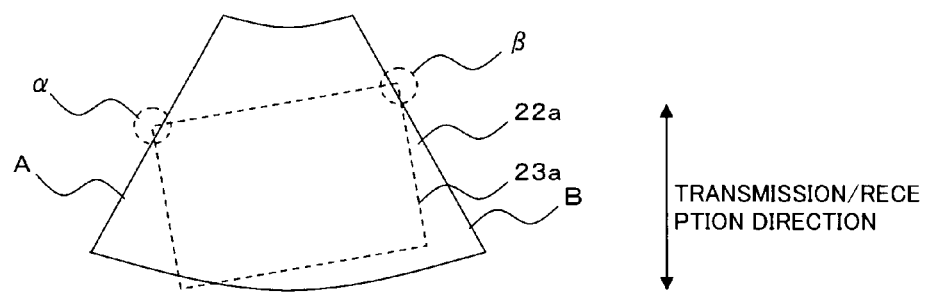
Figure 7:
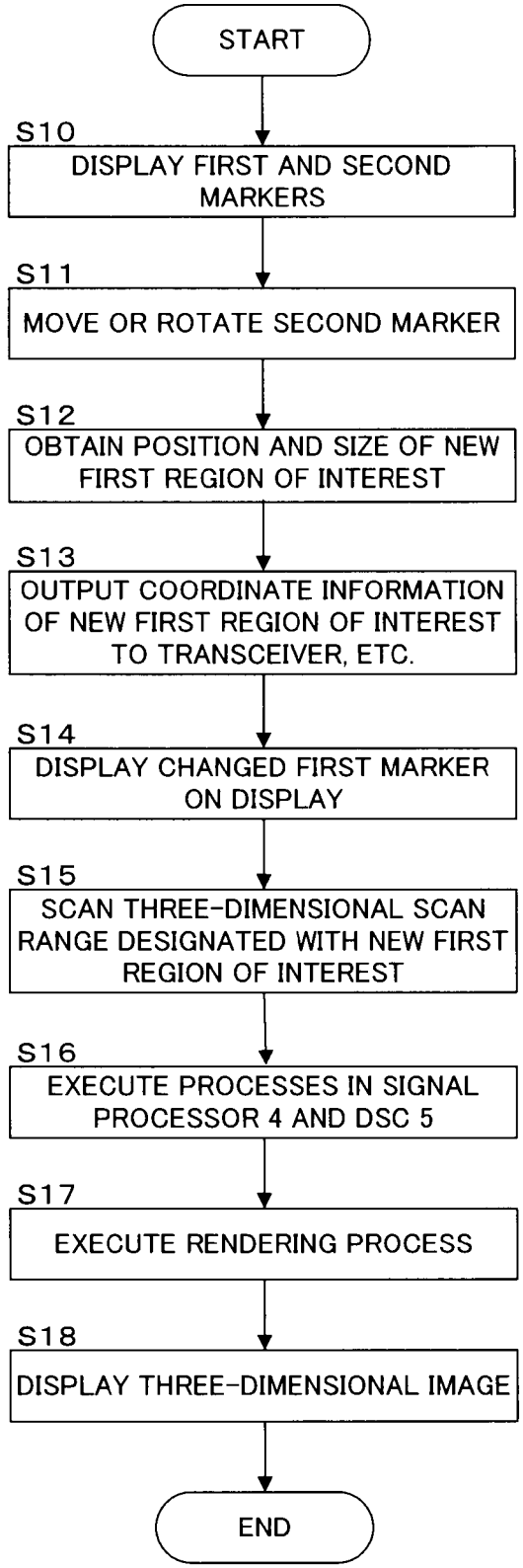
FIG. 7 is a flow chart showing a series of operations by the ultrasound imaging apparatus according to the second embodiment of the present invention.
Figure 8:
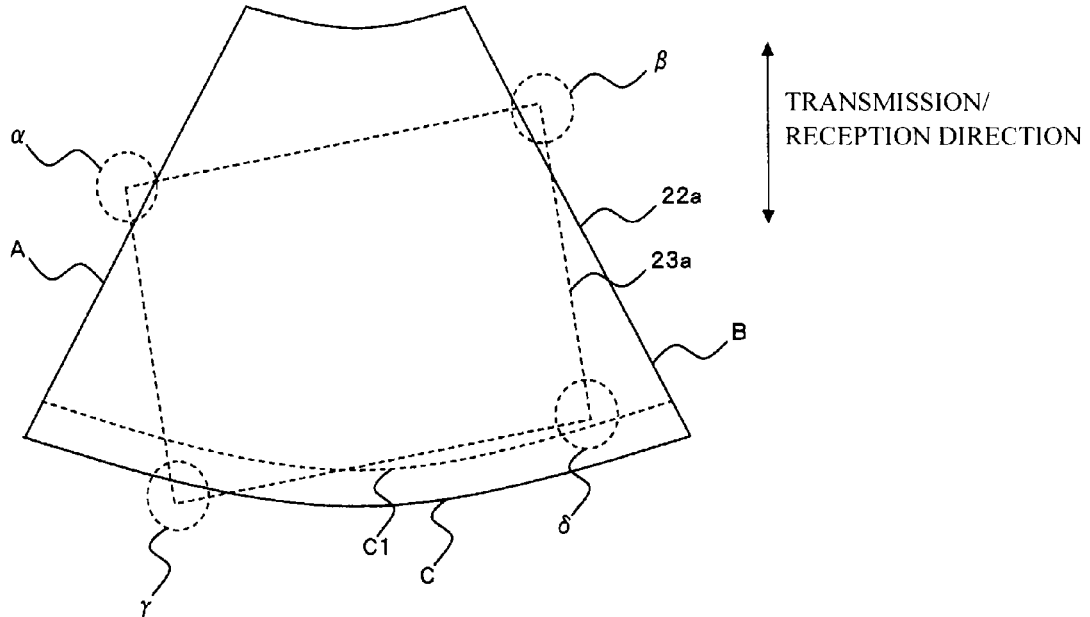
FIG. 8 is a schematic view for describing a process of obtaining a new three-dimensional scan range in the ultrasound imaging apparatus according to the second embodiment of the present invention.
Figure 9A:
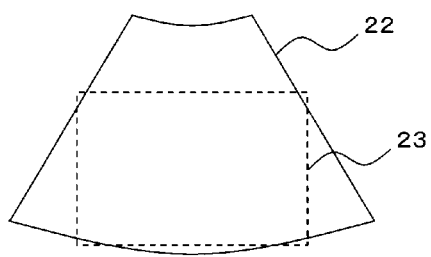
FIGS. 9A through 9E are schematic views for describing a process of obtaining a new region of interest (ROI) in an ultrasound imaging apparatus according to a third embodiment of the present invention.
Figure 9B:
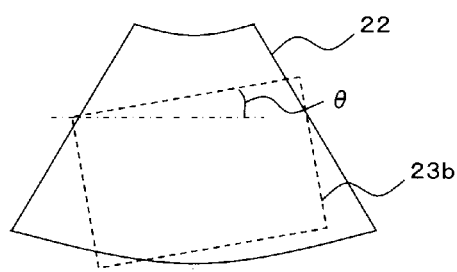
Figure 9C:
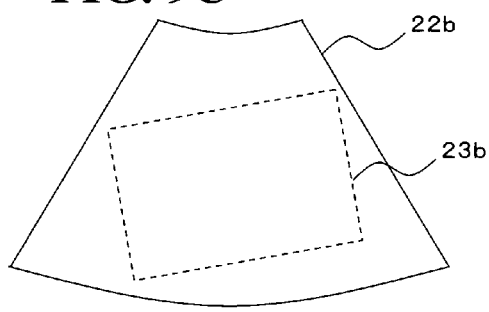
Figure 9D:
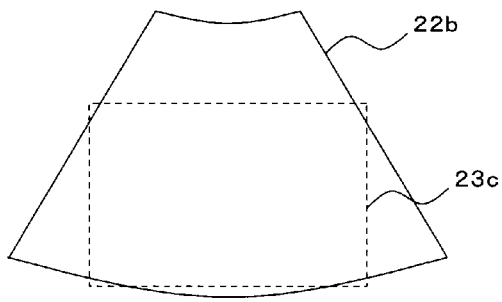
Figure 9E:
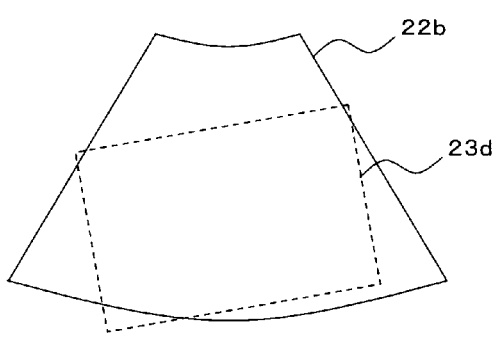
Figure 10:
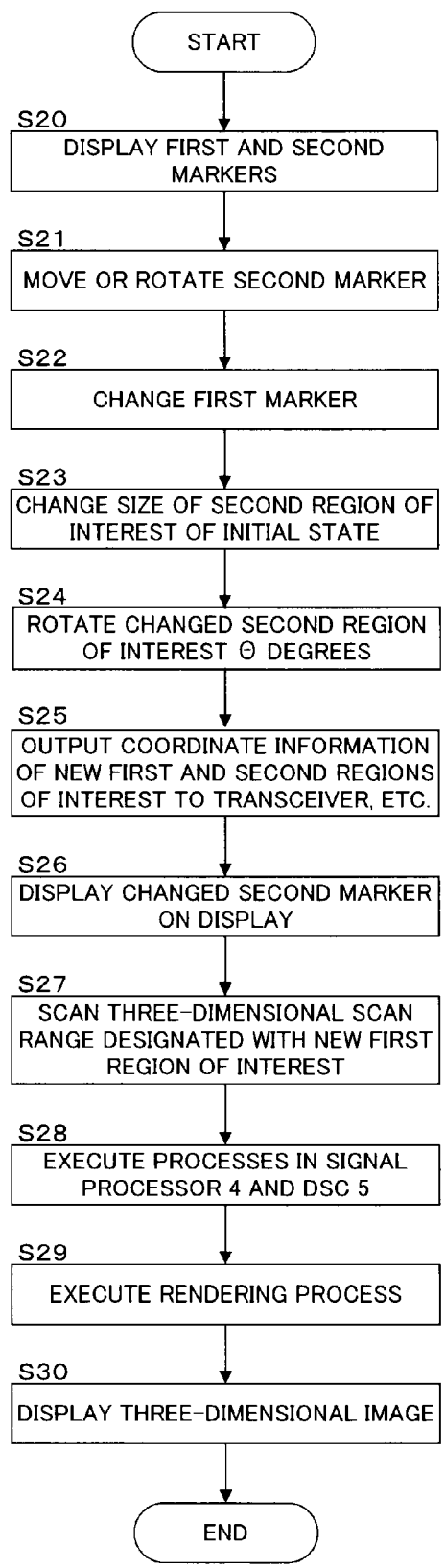
FIG. 10 is a flow chart for describing a series of operations by the ultrasound imaging apparatus according to the third embodiment of the present invention.

DESCRIPTION OF REFERENCE NUMERALS AND SYMBOLS 1 ultrasound imaging apparatus
2 ultrasound probe
3 transceiver
4 signal processor
5 DSC
6 first frame memory
7 image processor
8 second frame memory
9 display controller
10 display
11 operation part
12 marker generator
20 tomographic image
21 infant image
22, 22a, 22b first marker (marker indicating first region of interest)
23, 23a, 23b, 23c, 23d second marker (marker indicating second region of interest)

The invention claimed is:

1. An ultrasound imaging apparatus, comprising:
a scanner configured to transmit ultrasound waves to a subject and receive reflected waves from the subject;
an image generator configured to generate tomographic image data based on the reflected waves;
a marker generator configured to generate a first marker of a first scan range and a second marker of a second scan range; and
a display controller configured to cause a display to display each of a tomographic image based on the tomographic image data, the first marker, and the second marker, and cause the display to display both of the first marker and the second marker so as to be superimposed on the tomographic image in a state that the second marker is included in the first scan range of the first marker, wherein:
the scanner is configured to execute scan with ultrasound waves on the range specified based on the first marker; and
the image generator is configured to generate three-dimensional image data based on, of data acquired in the scan, data included in a range specified based on the second marker.

2. The ultrasound imaging apparatus according to claim 1, wherein:
the marker generator is configured to generate a new second marker rotated in accordance with an instruction to rotate the second marker;
the display controller is configured to cause the display to display the new second marker so as to be superimposed on the tomographic image;
the scanner is configured to execute scan with ultrasound waves on the range specified based on the first marker; and
the image generator is configured to generate three-dimensional image data based on, of data acquired in the scan, data included in a range specified based on the new second marker.

3. The ultrasound imaging apparatus according to claim 1, wherein:
the scanner is configured to execute scan with ultrasound waves on a three-dimensional range specified based on the first marker; and
the image generator is configured to generate three-dimensional image data based on data included in a three-dimensional range specified based on the second marker.

4. The ultrasound imaging apparatus according to claim 1, wherein:
the scanner is configured to execute scan while changing an ultrasound scan range in accordance with movement of the second marker.

5. The ultrasound imaging apparatus according to claim 4, wherein:
the scanner is configured to execute scan while changing, of the ultrasound scan range, a range in a direction substantially orthogonal to an ultrasound transmission direction in accordance with movement of the second marker.

6. The ultrasound imaging apparatus according to claim 4, wherein:
the scanner is configured to execute scan while changing an ultrasound transmission depth in accordance with movement of the second marker.

7. The ultrasound imaging apparatus according to claim 1, wherein:
the marker generator is configured to generate a new first marker with a range changed in accordance with movement of the second marker;

the display controller is configured to cause the display to display the new first marker; and the scanner is configured to execute scan with ultrasound waves on the range specified based on the new first marker.

8. The ultrasound imaging apparatus according to claim 7, wherein:
the first marker is configured to have sides along an ultrasound transmission direction; and
the marker generator is configured to generate a new first marker with a range changed so that the sides of the first marker along the ultrasound transmission direction are located near ends of the second marker.

9. The ultrasound imaging apparatus according to claim 7, wherein:
the first marker is configured to have sides substantially orthogonal to an ultrasound transmission direction; and
the marker generator is configured to generate a new first marker with a range changed so that, of the substantially orthogonal sides, the side deeper in the transmission direction is located near a part deepest in the transmission direction of the second marker.

10. The ultrasound imaging apparatus according to claim 1, wherein:
the marker generator is configured to generate a new second marker with a range changed in accordance with change of the range of the first marker.

11. The ultrasound imaging apparatus according to claim 10, wherein:
when the second marker is rotated and moreover the range of the first marker is changed, the marker generator is configured to change the range of the second marker before rotated in accordance with the change of the range of the first marker, and generate a new second marker by rotating the second marker with the range changed.

12. The ultrasound imaging apparatus according to claim 1, wherein:
the marker generator is configured to generate the second marker having a rectangular shape or an elliptic shape.

13. A method for acquiring an ultrasound image, comprising:
transmitting ultrasound waves to a subject and receiving reflected waves from the subject to generate tomographic image data based on the reflected waves;
causing a display to display each of a tomographic image based on the tomographic image data, a first marker of a first scan range, and a second marker of a second scan range, and causing the display to display both of the first marker and the second marker so as to be superimposed on the tomographic image in a state that the second marker is included in the first scan range of the first marker;
executing scan with ultrasound waves on the range specified based on the first marker; and
generating three-dimensional image data based on, of data acquired in the scan, data included in a range specified based on the second marker.

14. The method for acquiring an ultrasound image according to claim 13, wherein:
a new second marker obtained by rotating in accordance with an instruction to rotate the second marker is generated, and the new second marker is superimposed on the tomographic image and displayed on the display; and
three-dimensional image data is generated based on, of the data acquired in the scan, data included in a range specified based on the new second marker.

* * * * *